United States Patent
Nakamura et al.

(10) Patent No.: US 7,790,913 B2
(45) Date of Patent: Sep. 7, 2010

(54) FULLERENE DERIVATIVE AND METHODS FOR PRODUCING SAME

(75) Inventors: Eiichi Nakamura, Tokyo (JP); Yutaka Matsuo, Tokyo (JP); Takahiro Nakae, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 22 days.

(21) Appl. No.: 12/294,002

(22) PCT Filed: Mar. 15, 2007

(86) PCT No.: PCT/JP2007/055933

§ 371 (c)(1),
(2), (4) Date: Sep. 22, 2008

(87) PCT Pub. No.: WO2007/111226

PCT Pub. Date: Oct. 4, 2007

(65) Prior Publication Data

US 2009/0118527 A1    May 7, 2009

(30) Foreign Application Priority Data

Mar. 24, 2006 (JP) .............................. 2006-081836

(51) Int. Cl.
*C07F 17/02* (2006.01)
*C07F 15/00* (2006.01)

(52) U.S. Cl. .................. 556/143; 556/136; 556/140; 977/734; 977/740

(58) Field of Classification Search ................ 556/136, 556/140, 143; 977/734, 740
See application file for complete search history.

(56) References Cited

FOREIGN PATENT DOCUMENTS

| JP | 10-167994 | 6/1998 |
| JP | 11-255509 | 9/1999 |

OTHER PUBLICATIONS

Matsuo et al., Journal of American Chemical Society, vol. 126, No. 2, pp. 432-433 (2004).*
Sawamura et al., Journal of Organometallic Chemistry, vol. 652, pp. 31-35 (2002).*
Journal of the American Chemical Society, vol. 125(19), pp. 13974-13975, 2003.
Journal of the American Chemical Society, vol. 124(32), pp. 9354-9355, 2002.
Organic Letters, vol. 8(7), pp. 1463-1466, 2006.
Shadon Hojin CSJ, The Chemical Society of Japan, The Fifth Series of Experimental Chemistry, Maruzen Co., Ltd., Sep. 10, 2004, pp. 77-79, and 280-282 with partial English translation.
Single-step synthesis of pentaaryl-monohydro[60]fullerenes through fivefold addition of organocopper reagent to $C_{60}$, Masaya Sawamura et al., Journal of Organometallic Chemistry 599 (2000) pp. 32-36.
Synthesis of $C_5$-Symmetric Functionalized [60]Fullerenes by Copper-Mediated 5-Fold Addition of Reformatsky Reagents, Takahiro Nakae et al., Orgaitc Letters 2008 vol. 10, No. 4, pp. 621-623.
Regioselective penta-addition of 1-alkenyl copper reagents to [60] fullerene. Synthesis of penta-alkenyl FCp ligand, Masaya Sawamura et al., Journal of Organometallic Chemistry 652 (2002) pp. 31-35.
Selective Multiaddition of Organocopper Reagents to Fullerenes, Yutaka Matsuo et al., Chem. Rev. 2008, 108, pp. 3016-3028.

* cited by examiner

*Primary Examiner*—Porfirio Nazario Gonzalez
(74) *Attorney, Agent, or Firm*—Morgan Lewis & Bockius LLP

(57) ABSTRACT

The present invention provides a method for producing a fullerene derivative comprising reacting: a fullerene; an organometallic reagent (A) comprising B, Al, Zn, Sn, Pb, Te, Ti, Mn, Zr or Sm; and a copper compound (B).

21 Claims, No Drawings

FULLERENE DERIVATIVE AND METHODS FOR PRODUCING SAME

CROSS REFERENCE TO RELATED APPLICATIONS

This application is a U.S. National Phase Application of International Application Number PCT/JP2007/055933, filed Mar. 15, 2007, which claims the benefit of Japanese Patent Application No. 2006-081836, filed Mar. 24, 2006, each of which is incorporated by reference in its entirety.

TECHNICAL FIELD

The present invention relates to fullerene derivatives. Further, the present invention relates to a method for producing the aforementioned fullerene derivatives using an organometallic reagent and a copper compound.

BACKGROUND ART

Since the method for synthesizing a carbon cluster (hereinafter also referred to as "fullerene"), in which carbon atoms are arranged to form a spherical shape or a rugby ball shape, was established, fullerene has been energetically studied. As a result, many fullerene derivatives have been synthesized.

With respect to specific examples of such fullerene derivatives, methods for synthesizing a fullerene derivative, in which 5 organic groups bind to a fullerene skeleton (hereinafter also just referred to as "penta(organo)fullerene derivative"), have been reported (e.g., Japanese Laid-Open Patent Publication No. Hei 10-167994; Japanese Laid-Open Patent Publication No. Hei 11-255509; J. Am. Chem. Soc., 118, 12850 (1996); Org. Lett., 2, 1919 (2000); and Chem. Lett., 1098 (2000)).

As a method for producing a penta(organo)fullerene derivative, for example, it is known that, by reacting an organocopper reagent prepared using a phenyl Grignard reagent and $CuBr \cdot S(CH_3)_2$ with fullerene $C_{60}$, a phenylated fullerene derivative, in which phenyl groups constituting the phenyl Grignard reagent are regioselectively added to surround one 5-membered ring of fullerene $C_{60}$ ($C_{60}Ph_5H$), can be quantitatively obtained (e.g., Japanese Laid-Open Patent Publication No. 10-167994).

However, since compounds having a substituent such as a carboxyl group and an ester group are active against Grignard reagents, it is difficult to prepare Grignard reagents having such a substituent. Therefore, it has been impossible to use methods for conveniently synthesizing a fullerene derivative having a substituent such as a carboxyl group and an ester group using a Grignard reagent having such a substituent.

As a result, in order to synthesize a fullerene derivative having such a substituent, it has been necessary to use time-consuming methods such as: methods for producing a penta(organo)fullerene derivative by reacting a large excess of bromomalonate derivative with fullerene in a multistage manner (Angew. Chem. Int. Ed. Engl., 33, 2339 (1994); Angew. Chem. Int. Ed. Engl., 34, 1607 (1995); etc.); and a multistage synthesis method comprising the step of reacting $C_{60}I_6$ with benzene to cause electrophilic substitution (J. Chem. Soc., Chem. Commun. 1464 (1994)); etc. In addition, in the case of these methods for producing fullerene derivatives, there are problems that it is very difficult to regioselectively obtain a penta(organo)fullerene derivative, and that the yield of fullerene derivative is low.

DISCLOSURE OF THE INVENTION

Under the above-described circumstances, for example, a method for conveniently synthesizing a fullerene derivative having a substituent such as an ester group and a carboxyl group is desired. Further, for example, conveniently obtaining a penta(organo)fullerene derivative to which a substituent is regioselectively added is desired.

The present inventors found a novel fullerene derivative and a method for conveniently producing a fullerene derivative comprising reacting fullerene with an organometallic reagent (A) and a copper compound (B), and completed the present invention based on this finding. The present invention provides fullerene derivatives, methods for producing fullerene derivatives, etc. as follows.

[1] A method for producing a fullerene derivative comprising reacting:
 a fullerene;
 an organometallic reagent (A) comprising: a substituted or unsubstituted alkyl group, a substituted or unsubstituted alkenyl group, a substituted or unsubstituted alkynyl group, a substituted or unsubstituted aryalkyl group or a substituted or unsubstituted aryl group; and B, Al, Zn, Sn, Pb, Te, Ti, Mn, Zr or Sm; and
 a copper compound (B).

[2] A method for producing a fullerene derivative comprising reacting:
 a fullerene;
 an organometallic reagent (A) comprising: a substituted or unsubstituted alkyl group, a substituted or unsubstituted alkenyl group, a substituted or unsubstituted alkynyl group, a substituted or unsubstituted aryalkyl group or a substituted or unsubstituted aryl group; and Al, Zn, Sn or Pb; and
 a copper compound (B).

[3] A method for producing a fullerene derivative comprising reacting:
 a $C_{60}$ fullerene;
 an organometallic reagent (A) comprising: an alkyl group which may have one or more substituents selected from the group consisting of an ester group, an amide group, a cyano group and a halogen atom, an alkenyl group which may have one or more substituents selected from the group consisting of an ester group, an amide group, a cyano group and a halogen atom, or an aryl group which may have one or more substituents selected from the group consisting of an ester group, an amide group, a cyano group and a halogen atom; and Zn; and
 a monovalent or divalent copper compound (B).

[4] The method for producing a fullerene derivative according to any one of items [1] to [3], wherein the fullerene derivative is represented by the following formula (1):

$$C_n(R^4)_m(R^5)_p \qquad (1)$$

wherein n is an even number of 60 or more; m is an integer from 3 to 10; p is 1 or 2; each $R^4$ is independently a hydrogen atom, a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group); and $R^5$ is a hydrogen atom or a $C_1$-$C_{20}$ hydrocarbon group.

[5] The method for producing a fullerene derivative according to any one of items [1] to [3], wherein the fullerene derivative is a fullerene derivative $C_{60}(R^4)_5R^5$ represented by the following formula (2):

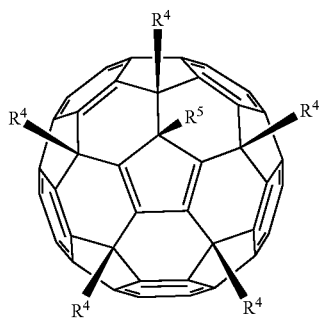

(2)

wherein each 4 is independently a hydrogen atom, a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group), or a substituted or unsubstituted arylsulfonyl group (—$SO_2Y^4$: in the formula, $Y^4$ is a substituted or unsubstituted $C_6$-$C_{18}$ aryl group); and $R^5$ is a hydrogen atom or a $C_1$-$C_{20}$ hydrocarbon group.

[6] The method for producing a fullerene derivative according to item [4] or [5], wherein $R^4$ has one or more substituents selected from the group consisting of an ester group, a carboxyl group, an amide group, an alkyne group, a trimethylsilyl group, a trimethylsilylethynyl group, an aryl group, an amino group, a phosphonyl group, a thio group, a carbonyl group, a nitro group, a sulfo group, an imino group, a halogeno group, and an alkoxy group.

[7] The method for producing a fullerene derivative according to item [4] or [5], wherein $R^4$ has one or more substituents selected from the group consisting of an ester group, an amide group, an alkyne group, a trimethylsilyl group, a trimethylsilylethynyl group, and an aryl group.

[8] The method for producing a fullerene derivative according to any one of items [4] to [7], wherein $R^5$ is a hydrogen atom or a $C_1$-$C_{20}$ alkyl group.

[9] The method for producing a fullerene derivative according to any one of items [1] to [3], wherein the fullerene derivative is represented by the following formula (3);

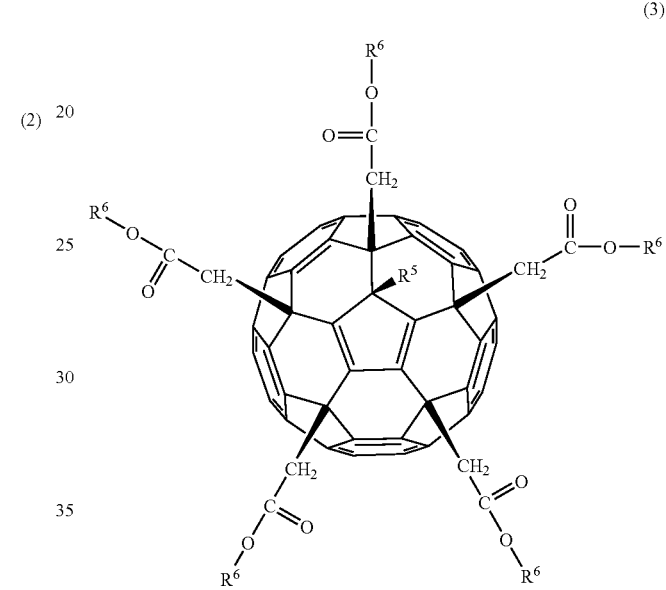

(3)

wherein $R^5$ is a hydrogen atom or a substituted or unsubstituted $C_1$-$C_{20}$ hydrocarbon group; and each $R^6$ is independently a hydrogen atom or a substituted or unsubstituted $C_1$-$C_{20}$ hydrocarbon group.

[10] The method for producing a fullerene derivative according to item [9], wherein $R^5$ is a hydrogen atom or a substituted or unsubstituted $C_1$-$C_{20}$ alkyl group.

[11] The method for producing a fullerene derivative according to item [9] or [10], wherein $R^6$ is a hydrogen atom a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group.

[12] The method for producing a fullerene derivative according to any one of items [1] to [11], wherein an organic group included in the organometallic reagent (A) is a methyl group, an ethyl group, an isopropyl group, a butyl group or a phenyl group.

[13] The method for producing a fullerene derivative according to any one of items [1] to [12], wherein the copper compound (B) is $CuBr \cdot S(CH_3)_2$.

[14] A fullerene derivative represented by the following formula (3):

(3)

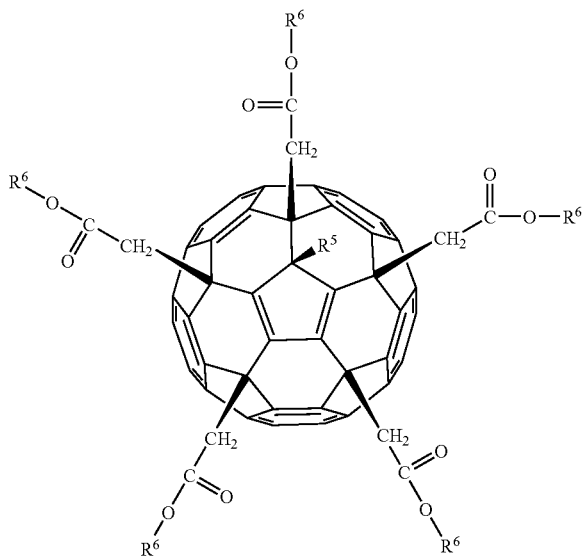

wherein $R^5$ is a hydrogen atom or a substituted or unsubstituted $C_1$-$C_{20}$ hydrocarbon group; and each $R^6$ independently a hydrogen atom or a substituted or unsubstituted $C_1$-$C_{20}$ hydrocarbon group.

[15] The fullerene derivative according to item [14], wherein $R^5$ is a hydrogen atom or a substituted or unsubstituted $C_1$-$C_{20}$ alkyl group.

[16] The fullerene derivative according to item [14] or [15], wherein $R^6$ is a hydrogen atom, a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group.

[17] A fullerene derivative represented by the following formula (4):

(4)

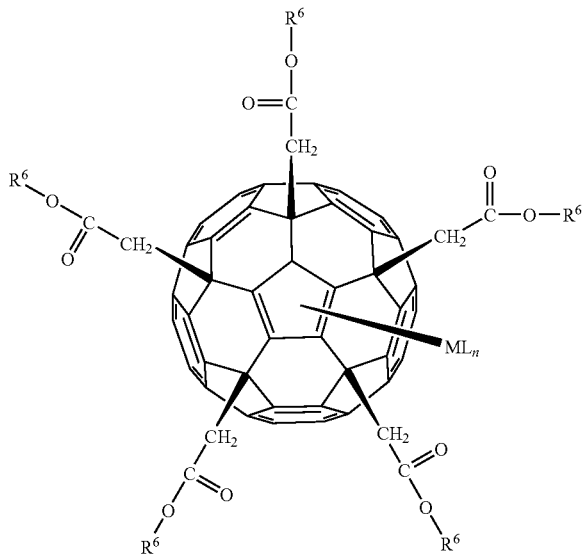

wherein each $R^6$ is independently a hydrogen atom or a substituted or unsubstituted $C_1$-$C_{20}$ hydrocarbon group; M is a metallic atom; L is a ligand of M; and n is the number of Ls.

[18] The fullerene derivative according to item [17], wherein $R^6$ is a hydrogen atom, a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group.

[19] The fullerene derivative according to item [17] or [18], wherein M is a transition metal.

[20] The fullerene derivative according to item [17] or [18], wherein M is a group 8-10 transition metal.

[21] The fullerene derivative according to item [17] or [18], wherein: M is Fe, Ru, or Os; n is an integer from 0 to 5; and L is a halogen atom, alkoxy group, alkyl group, alkyne group or cyclopentadienyl group.

When using the method for producing a fullerene derivative related to the preferred embodiment of the present invention, for example, it is possible to conveniently obtain a fullerene derivative having a functional group such as an ester group, an amide group, an alkyne group and a trimethylsilyl group as a substituent, When using the method for producing a fullerene derivative related to the preferred embodiment of the present invention, for example, it is possible to conveniently obtain a penta(organo)fullerene derivative to which a substituent is regioselectively added. Moreover, when using the method for producing a fullerene derivative related to the preferred embodiment of the present invention, for example, it is possible to obtain a fullerene derivative in good yield.

BEST MODE FOR CARRYING OUT THE INVENTION

1. Fullerene Derivative of the Present Invention

As described above, the fullerene derivative of the present invention is represented by the above-described formula (1). The fullerene derivative of the present invention can be produced using, for example, the method for producing a fullerene derivative of the present invention.

In this regard, "fullerene" is a general term for carbon clusters which are formed by arranging carbon atoms in a spherical shape or a rugby ball shape (see Gendai-Kagaku, June 2000, page 46; and Chemical Reviews, 98, 2527 (1998)). Examples thereof include fullerene $C_{60}$ (so-called buckminsterfullerene), fullerene $C_{70}$, fullerene $C_{76}$, fullerene $C_{78}$, fullerene $C_{82}$, fullerene $C_{84}$, fullerene $C_{90}$, fullerene $C_{94}$, and fullerene $C_{96}$.

In formula (1), n is an even number of 60 or more, which depends on the type of fullerene used as a raw material for producing a fullerene derivative. Specifically, n is an even number such as 60, 70, 76, 78, 82, 84, 90, 94 and 96.

In formula (1), m is an integer from 3 to 10, and preferably an integer from 5 to 10. When m is 3 to 5, p is preferably 1. When m is 6, 8 or 10, p is preferably 2. When m is 7 or 9, p is preferably 1.

Further, in formula (1), each $R^4$ is a hydrogen atom, a substituted or unsubstituted $C_1$-$C_{20}$ hydrocarbon group, a substituted or unsubstituted $C_1$-$C_{20}$ alkoxy group, a substituted or unsubstituted $C_6$-$C_{20}$ aryloxy group, a substituted or unsubstituted amino group, a substituted or unsubstituted silyl group, a substituted or unsubstituted alkylthio group (—$SY^1$: in the formula, $Y^1$ is a substituted or unsubstituted $C_1$-$C_{20}$ alkyl group), a substituted or unsubstituted arylthio group (—$SY^2$: in the formula, $Y^2$ is a substituted or unsubstituted $C_6$-$C_{18}$ aryl group), a substituted or unsubstituted alkylsulfonyl group (—$SO_2Y^3$: in the formula, $Y^3$ is a substituted or unsubstituted $C_1$-$C_{20}$ alkyl group) or a substituted or unsubstituted arylsulfonyl group (—$SO_2Y^4$: in the formula, $Y^4$ is a substituted or unsubstituted $C_6$-$C_{18}$ aryl group). $R^4$s may be the same or different.

Further, in formula (1), $R^5$ is a hydrogen atom or a $C_1$-$C_{20}$ alkyl group.

In the fullerene derivative obtained by the production method of the present invention, groups to be added to a fullerene skeleton ($R^4$, $R^5$) can be regioselectively added to the fullerene skeleton. For example, when using fullerene $C_{60}$ as a raw material, $R^4$s can be added to the fullerene skeleton to surround one 5-membered ring of fullerene $C_{60}$, and $R^5$ can be added to one carbon of the 5-membered ring.

In the present specification, the hydrocarbon group of the "$C_1$-$C_{20}$ hydrocarbon group" may be a saturated or unsaturated acyclic group or a saturated or unsaturated cyclic group. When the $C_1$-$C_{20}$ hydrocarbon group is acyclic, it may be linear or branched. The "$C_1$-$C_{20}$ hydrocarbon group" includes $C_1$-$C_{20}$ alkyl group, $C_2$-$C_{20}$ alkenyl group, $C_2$-$C_{20}$ alkynyl group, $C_4$-$C_{20}$ alkyldienyl group, $C_6$-$C_{18}$ aryl group, $C_7$-$C_{20}$ alkylaryl group, $C_7$-$C_{20}$ arylalkyl group, $C_4$-$C_{20}$ cycloalkyl group, $C_4$-$C_{20}$ cycloalkenyl group, and ($C_3$-$C_{10}$ cycloalkyl) $C_1$-$C_{10}$ alkyl group.

In the present specification, the "$C_1$-$C_{20}$ alkyl group" is preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, the "$C_2$-$C_{20}$ alkenyl group" is preferably $C_2$-$C_{10}$ alkenyl group, and more preferably $C_2$-$C_6$ alkenyl group. Examples of alkenyl groups include, but are not limited to, vinyl, allyl, propenyl, isopropenyl, 2-methyl-1-propenyl, 2-methylallyl, and 2-butenyl.

In the present specification, the "$C_2$-$C_{20}$ alkynyl group" is preferably $C_2$-$C_{10}$ alkynyl group, and more preferably $C_2$-$C_6$ alkynyl group. Examples of alkynyl groups include, but are not limited to, ethynyl, propynyl, and butynyl.

In the present specification, the "$C_4$-$C_{20}$ alkyldienyl group" is preferably $C_4$-$C_{10}$ alkyldienyl group, and more preferably $C_4$-$C_6$ alkyldienyl group. Examples of alkyldienyl groups include, but are not limited to 1,3-butadienyl.

In the present specification, the "$C_6$-$C_{18}$ aryl group" is preferably $C_6$-$C_{10}$ aryl group. Examples of aryl groups include, but are not limited to, phenyl, 1-naphthyl, 2-naphthyl, indenyl, biphenylyl, anthryl, and phenanthryl.

In the present specification, the "$C_7$-$C_{20}$ alkylaryl group" is preferably $C_7$-$C_{12}$ alkylaryl group. Examples of alkylaryl groups include, but are not limited to, o-tolyl, m-tolyl, p-tolyl, 2,3-xylyl, 2,4-xylyl, 2,5-xylyl, o-cumenyl, m-cumenyl, p-cumenyl, and mesityl.

In the present specification, the "$C_7$-$C_{20}$ arylalkyl group" is preferably $C_7$-$C_{12}$ arylalkyl group. Examples of arylalkyl groups include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, and 5-phenylpentyl.

In the present specification, the "$C_4$-$C_{20}$ cycloalkyl group" is preferably $C_4$-$C_{10}$ cycloalkyl group. Examples of cycloalkyl groups include, but are not limited to, cyclopropyl, cyclobutyl, cyclopentyl, and cyclohexyl.

In the present specification, the "$C_4$-$C_{20}$ cycloalkenyl group" is preferably $C_4$-$C_{10}$ cycloalkenyl group. Examples of cycloalkenyl groups include, but are not limited to, cyclopropenyl, cyclobutenyl, cyclopentenyl, and cyclohexenyl.

In the present specification, the "$C_1$-$C_{20}$ alkoxy group" is preferably $C_1$-$C_{10}$ alkoxy group, and more preferably $C_1$-$C_6$ alkoxy group. Examples of alkoxy groups include, but are not limited to, methoxy, ethoxy, propoxy, butoxy, and pentyloxy.

In the present specification, the "$C_6$-$C_{20}$ aryloxy group" is preferably $C_6$-$C_{10}$ aryloxy group. Examples of aryloxy groups include, but are not limited to, phenyloxy, naphthyloxy, and biphenyloxy.

In the present specification, in "alkylthio group (—$SY^1$: in the formula, $Y^1$ is a substituted or unsubstituted $C_1$-$C_{20}$ alkyl group)" and "alkylsulfonyl group (—$SO_2Y^3$: in the formula, $Y^3$ is a substituted or unsubstituted $C_1$-$C_{20}$ alkyl group)", $Y^1$ and $Y^3$ are preferably $C_1$-$C_{10}$ alkyl group, and more preferably $C_1$-$C_6$ alkyl group. Examples of alkyl groups include, but are not limited to, methyl, ethyl, propyl, isopropyl, n-butyl, sec-butyl, tert-butyl, pentyl, hexyl, and dodecanyl.

In the present specification, in "arylthio group (—$SY^2$: in the formula, $Y^2$ is a substituted or unsubstituted $C_6$-$C_{18}$ aryl group)" and "arylsulfonyl group (—$SO_2Y^4$: in the formula, $Y^4$ is a substituted or unsubstituted $C_6$-$C_{18}$ aryl group)", $Y^2$ and $Y^4$ are preferably $C_6$-$C_{10}$ aryl group. Examples of aryl groups include, but are not limited to, phenyl, 1-naphthyl, 2-naphthyl, indenyl, biphenylyl, anthryl, and phenanthryl.

"$C_1$-$C_{20}$ hydrocarbon group," "$C_1$-$C_{20}$ alkoxy group," "$C_6$-$C_{20}$ aryloxy group," "amino group," "silyl group," "alkylthio group," "arylthio group," "alkylsulfonyl group," and "arylsulfonyl group" may be substituted. Examples of substituents in these cases include ester group, carboxyl group, amide group, alkyne group, trimethylsilyl group, amino group, phosphonyl group, thio group, carbonyl group, nitro group, sulfo group, imino group, halogeno group, and alkoxy group. In these cases, one or more substituents (up to the maximum possible number) may be introduced into replaceable positions, and preferably, 1 to 4 substituents may be introduced. When the number of substituents is 2 or more, the substituents may be the same or different. Further, substituents include halogen atoms such as F, Cl, Br and I.

In the present specification, examples of "substituted or unsubstituted amino group" include, but are not limited to, amino, dimethylamino, methylamino, methylphenylamino, and phenylamino.

In the present specification, examples of "substituted or unsubstituted silyl group" include, but are not limited to, dimethylsilyl, diethylsilyl, trimethylsilyl, triethylsilyl, trimethoxysilyl, triethoxysilyl, diphenylmethylsilyl, triphenylsilyl, triphenoxysilyl, dimethylmethoxysilyl, dimethylphenoxysilyl, and methylmethoxyphenyl.

In the present specification, examples of "aromatic group" include phenyl group, biphenyl group, and terphenyl group.

In the present specification, examples of "heterocyclic group" include thienyl group, pyrrolyl group, pyridyl group, bipyridyl group, oxazolyl group, oxadiazolyl group, thiazolyl group, thiadiazolyl group, and terthienyl group.

In the present specification, examples of "condensed polycyclic aromatic group" include fluorenyl group, naphthyl group, fluoranthenyl group, anthryl group, phenanthryl group, pyrenyl group, tetracenyl group, pentacenyl group, triphenylenyl group, and perirenyl group.

In the present specification, examples of "condensed polycyclic heterocyclic group" include carbazolyl group, acridinyl group and phenanthroryl group.

Further, examples of substituents which can be had by these "aromatic group," "heterocyclic group," "condensed polycyclic aromatic group" and "condensed polycyclic heterocyclic group" include, but are not limited to, $C_1$-$C_{10}$ hydrocarbon group (e.g., methyl, ethyl, propyl, butyl, phenyl naphthyl, indenyl, tolyl, xylyl and benzyl), $C_1$-$C_{10}$ alkoxy group (e.g., methoxy, ethoxy, propoxy and butoxy), $C_6$-$C_{10}$ aryloxy group (e.g., phenyloxy, naphthyloxy and biphenyloxy), amino group, hydroxyl group, halogen atom (e.g., fluorine, chlorine, bromine and iodine) and silyl group. In these cases, one or more substituents may be introduced into replaceable positions, and preferably, 1 to 4 substituents are introduced. When the number of substituents is 2 or more, the substituents may be the same or different.

Among fullerene derivatives represented by formula (1), fullerene derivatives represented by the above-described formula (3) are synthesized in good yield when using the production method of the present invention.

Further, the present invention provides fullerene derivatives represented by the above-described formula (4). The fullerene derivatives represented by formula (4) can be synthesized, for example, by employing a publicly-known method in which a metal complex such as $[CpFe(CO)_2]_2$ is added to the fullerene derivatives represented by formula (3) and the mixture is heated.

2. Production Method of Fullerene Derivative of the Present Invention

The method for producing the fullerene derivative of the present invention is characterized in that a fullerene, an organometallic reagent (A) and a copper compound (B) are reacted to synthesize a fullerene derivative.

2.1. Fullerene

Examples of fullerenes to be used in the method for producing the fullerene derivative of the present invention include, but are not particularly limited to, fullerene $C_{60}$ (so-called "buckminsterfullerene"), fullerene $C_{70}$, fullerene $C_{76}$, fullerene $C_{78}$, fullerene $C_{82}$, fullerene $C_{84}$, fullerene $C_{90}$, fullerene $C_{94}$, and fullerene $C_{96}$. Among these fullerenes, it is preferable to use $C_{60}$ and $C_{70}$ in the production process of the present invention in terms of high availability

2.2 Organometallic Regent A

The organometallic reagent (A) to be used in the production method of the present invention is not particularly limited as long as it is a compound comprising: an organic group which may have a halogen atom; and B, Al, Zn, Sn, Pb, Te, Ti, Mn, Zr or Sm as a metal atom. Examples of organic groups include substituted or unsubstituted $C_1$-$C_{20}$ hydrocarbon groups, substituted or unsubstituted $C_1$-$C_{20}$ alkoxy groups, substituted or unsubstituted $C_6$-$C_{20}$ aryloxy groups, substituted or unsubstituted amino groups, substituted or unsubstituted silyl groups, substituted or unsubstituted alkylthio groups (—$SY^1$: in the formula, $Y^1$ is a substituted or unsubstituted $C_1$-$C_{20}$ alkyl group), substituted or unsubstituted arylthio groups (—$SY^2$: in the formula, $Y^2$ is a substituted or unsubstituted $C_6$-$C_{18}$ aryl group), substituted or unsubstituted alkylsulfonyl groups (—$SO_2Y^3$: in the formula, $Y^3$ is a substituted or unsubstituted $C_1$-$C_{20}$ alkyl group), and substituted or unsubstituted arylsulfonyl groups (—$SO_2Y^4$: in the formula, $Y^4$ is a substituted or unsubstituted $C_6$-$C_{18}$ aryl group). Among these organic groups, substituted or unsubstituted alkenyl groups, substituted or unsubstituted alkynyl groups, substituted or unsubstituted arylalkyl groups, substituted or unsubstituted aryl groups and the like are preferred.

Moreover, the aforementioned organic group may have substituents comprising functional groups such as an ester group, a carboxyl group, an amide group, an alkyne group, a trimethylsilyl group, a trimethylsilylethynyl group, an aryl group, an amino group, a phosphonyl group, a thio group, a carbonyl group, a nitro group, a sulfo group, an imino group, a halogeno group, and an alkoxy group. In terms of easiness of synthesis of the organometallic reagent (A), the organic group preferably comprises one or more functional groups selected from the group consisting of an ester group (e.g., an ethyl ester group and a methyl ester group), an amide group and a cyano group. In this case, when 2 or more functional groups are included in the organic group, they may be the same or different.

The halogen atom which may be included in the organic group is not particularly limited, and examples thereof include F, Cl, Br and I. Among these halogen atoms, F, Br or I is preferably included.

The metal atom to be included in the organometallic reagent (A) is B, Al, Zn, Sn, Pb, Te, Ti, Mn, Zr or Sm, and is preferably Al, Zn, Sn or Pb. Most preferably, the metal atom is Zn.

Moreover, the organometallic reagent (A) may have a plurality of organic groups.

Examples of organometallic reagents include compounds having a structure such as $R^1$-M-$R^2$ (in the formula, $R^1$ and $R^2$ are each independently an organic group, and M is a metal atom) and $R^1$-M-X (in the formula, $R^1$ is an organic group, M is a metal atom, and X is a halogen atom).

As the organometallic reagent (A), a commercially-available reagent can be used. Moreover, the organometallic reagent (A) can be prepared, for example, by employing a method in which: metal powder of Zn or the like is subjected to activation treatment; thereafter a desired organic halide or the like is added thereto; and the mixture is stirred at room temperature (for example, for about 2 hours).

2.3. Copper Compound (B)

The copper compound (B) to be used in the production method of the present invention is not particularly limited as long as it is a compound comprising an organic group and a copper atom. Preferably, the copper compound (B) is prepared from a monovalent or divalent copper compound. Among them, $CuBr.S(CH_3)_2$ is preferably used as the copper compound because purification is easily performed and purity can be improved.

Further, according to circumstances, in order to stabilize the copper compound (B), to improve solubility thereof or the like, an additive such as N,N-dimethylimidazolidinone (DMI) and N-butylpyrrolidone (NBT) can be suitably used.

2.4. Mixing Ratio, Etc.

In general, the organometallic reagent (A) is used in an amount of 5 to 50 equivalents, and preferably 10 to 30 equivalents of a fullerene as a raw material.

The amount of the copper compound (B) to be used is not particularly limited. However, the mixing ratio (molar ratio) of the organometallic reagent (A) to the copper compound (B) is preferably 8:1 to 1:2, more preferably 2:1 to 1:2, and most preferably about 1:1.

2.5. Reaction Conditions

Reaction of the fullerene, the organometallic reagent (A) and the copper compound (B) in the production method of the present invention is generally performed in an inert solvent such as toluene, tetrahydrofuran, dichlorobenzene, or a mixture thereof.

The reaction is preferably performed under ordinary pressure at a temperature in the range from −70° C. to 70° C., and more preferably at a temperature in the range from −50° C. to 50° C.

Further, reaction time depends on a solvent to be used, temperature, etc. In general, the reaction is performed for about several minutes to 5 hours, and preferably for about 10 minutes to 4 hours.

Termination of synthesis reaction of the fullerene derivative of the present invention can be carried out by adding an ammonium chloride solution or the like to the reaction system.

2.6. Isolation of Fullerene Derivative

The method for isolating the fullerene derivative from the synthesis reaction system in the present invention is not particularly limited. For example, a reaction solution is directly passed through a silica gel column to remove by-products such as inorganic substances. According to need, isolated substances are further purified by means of HPLC, usual column chromatography, etc., to improve purity of the fullerene derivative.

2.7. Conversion of Substituent Added to Fullerene Skeleton

A substituent added to a fullerene skeleton by the above-described synthesis reaction of the fullerene derivative of the present invention can be converted.

2.7.1. Method for Producing Fullerene Derivative to which Carboxyl Group is Added When a substituent added to the fullerene derivative obtained by means of the above-described synthesis reaction of the fullerene derivative of the present invention has an ester group, by employing a treatment in which a base such as Nab and NaOH is added to the fullerene derivative, the ester group can be converted into a carboxyl group.

Thus, the fullerene derivative to which the carboxyl group is added can be obtained.

2.8. Method for Producing Fullerene Derivative Obtained by Further Adding Alkyl Halide After the fullerene, the organometallic reagent and the copper compound are reacted, by further adding alkyl halide $R^3X^3(5)$ for further reaction, $R^3$ can be added to the fullerene derivative.

In the above-described formula (5) representing an alkyl halide to be added, $R^3$ represents a substituted or unsubstituted $C_1$-$C_{20}$ alkyl group, and $X^3$ represents a halogen atom.

The alkyl halide is not particularly limited as long as it satisfies the formula (5), but methyl iodide is most preferred.

An alkyl group to be added by the reaction can be regioselectively added to the fullerene skeleton. For example, when using fullerene $C_{60}$ as a raw material, an alkyl group can bind to a carbon which constitutes a 5-membered ring of the fullerene $C_{60}$ surrounded by 5 groups added.

3. Use of Fullerene Derivative Obtained by the Synthesis Reaction of the Present Invention A fullerene derivative having a substituent comprising a functional group obtained using the synthesis reaction of fullerene derivative of the present invention shows electrical properties and solubility in solvent which are different from those of conventional fullerene derivatives. Therefore, the fullerene derivative can be used as an electronic material such as an additive for a battery or a physiologically active substance though such use depends on the type of substituent.

Moreover, in particular, a fullerene derivative having a polar functional group such as an ester group, a carboxylic group, an alkyne group and a cyano group can be further subjected to a reaction on the polar functional group, and an additional substituent can be introduced therein. The fullerene derivative thus obtained can be bound to a polymer via a sigma bond, and therefore it is useful as a raw material.

Furthermore, for example, a metal complex of the fullerene derivative having a substituent comprising a functional group can be easily produced using a publicly-known method described, for example, in Japanese Laid-Open Patent Publication Nos. Hei 10-167994 and Hei 11-255509. In addition to electrical, photochemical and magnetic properties and the like derived from a fullerene skeleton, properties inherent to a metal atom can be imparted to the metal complex of the fullerene derivative, and therefore it is also useful as an element for electronic materials.

EXAMPLES

Hereinafter, the present invention will be specifically described by way of examples, but the present invention is not limited thereby.

Example 1

Production of $C_{60}(CH_2COOC_2H_5)_5H$

As indicated in the below Scheme 1, 2.0 g of fullerene $C_{60}$ was dissolved in 90 mL of orthodichlorobenzene under nitrogen atmosphere. To the mixture: 15 equivalents of ethoxycarbonylmethyl zinc bromide reagent $BrZnCH_2CO_2Et$ in THF solution (concentration: about 0.7M) as the organometallic reagent (A); 15 equivalents of copper (I) bromide-dimethylsulfide complex $CuBr.S(CH_3)_2$ as the copper compound (B); and 15 equivalents of N,N-dimethylimidazolidinone (4.75 g) were added, and the mixture was reacted at 25° C. 2.5 hours later, 2.0 n of saturated ammonium chloride solution was added to the mixture, and the reaction was terminated. The reaction product was diluted by adding 10 mL of deaerated toluene, and was passed through a short-pass silica gel column using toluene as a developing solvent to remove byproducts such as zinc salt. The solvent was distilled away, and 900 mL of methanol was added. A solid obtained from reprecipitation was subjected to filtration, and thereafter it was washed with methanol to obtain 2.94 g of penta(organo)[60] fullerene derivative $C_{60}(CH_2COOC_2H_5)_5H$ (isolated yield: 92%).

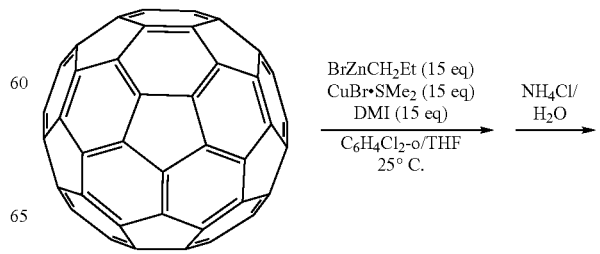

Scheme 1

-continued

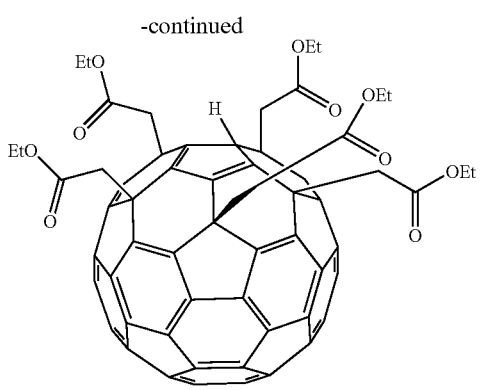

NMR data of the obtained product are as follows:

$^1$H NMR (CDCl$_3$) δ5.16 (s, 1H, CpH), 4.28 (q, J=7.16 Hz, 2H), 4.25 (q, J=7.16 Hz, 4H), 4.22 (q, J=7.16 Hz 4H), 3.71 (s, 2 f), 3.69 (d, J=14.3 Hz, 1H), 3.61 (d, J=14.6 Hz, 1H), 3.54 (d, J=14.6 Hz, 1H), 3.50 (d, J=14.3 Hz, 1H), 1.29 (t, J=7.16 Hz, 3H), 1.28 (t, J=7.16 Hz, 6H), 1.24 (t, J=7.16 Hz, 6H).

$^{13}$C NMR (CDCl$_3$) δ171.32, 170.49, 169.91, 155.17 (2C), 153.34 (2C), 152.15 (2C), 150.57 (2C), 148.59 (2C), 148.55 (2C), 148.24 (2C), 148.04 (2C), 148.00 (1C), 147.87 (2C), 147.63 (2C), 147.04 (2C), 146.92 (2C), 146.85 (1C), 146.52 (2C), 145.48 (2C), 145.13 (2C), 145.03 (20), 144.56 (2C), 144.13 (2C), 144.01 (20), 143.86 (2C), 143.85 (2C), 143.78 (2C), 143.69 (2C), 143.69 (2C), 143.57 (2C), 142.75 (2C), 61.23 (1C, CH$_2$CH$_3$), 61.18 (2C, CH$_2$CH$_3$), 61.14 (2C, CH$_2$CH$_3$), 57.56 (1C), 53.79 (2C), 52.39 (1C), 51.55 (2C), 44.58 (3C, CCO$_2$), 44.09 (2C, CO$_2$), 14.26 (20 CH$_3$CH$_3$), 14.22 (3C, CH$_2$CH$_3$).

Further, as indicated in the below Scheme 2, the fullerene derivative having an ester group (C$_{60}$(CH$_2$COOC$_2$H$_5$)$_5$H) obtained in Scheme 1 was dissolved in a phenylcyan solvent, [CpFe(CO)$_2$] was added thereto, and the mixture was reacted at 180° C. for 24 hours. As a result, single crystal of a buckyferrocene derivative having a functional group was successfully obtained.

Scheme 2

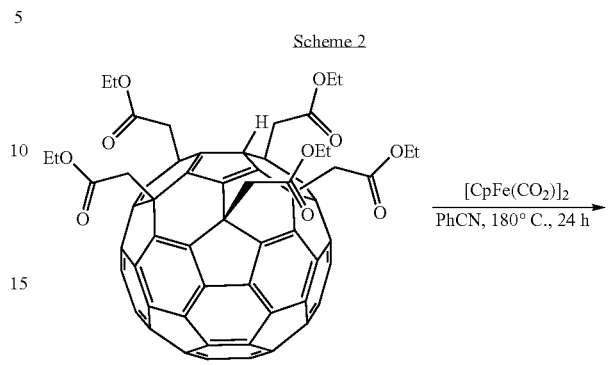

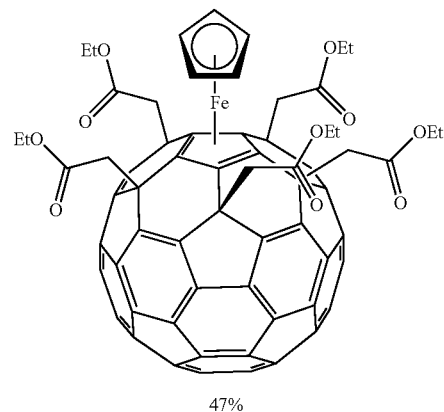

47%

The single crystal of the derivative was subjected to X-ray crystal structure analysis, and the structure was as shown below.

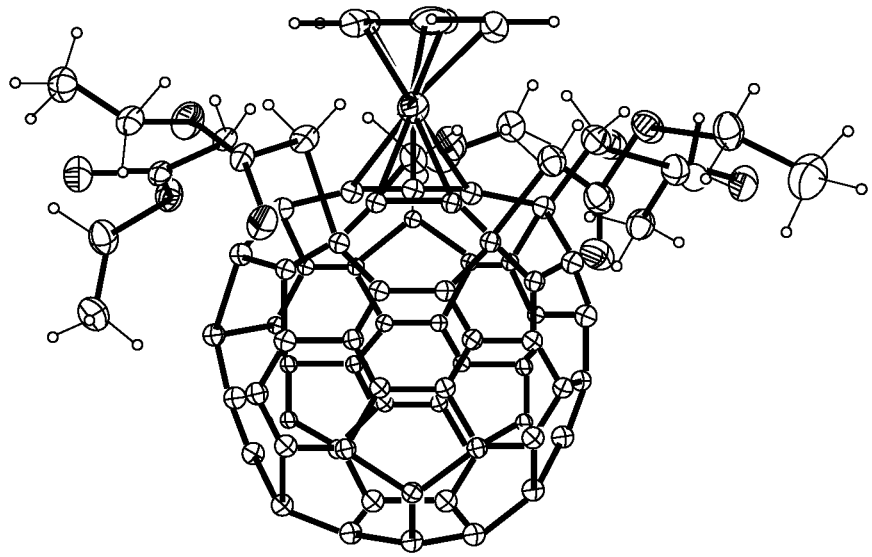

According to the X-ray crystal structure analysis, introduction of a methylene ester group and an iron complex was confirmed.

Example 2

Production of $C_{60}(C_6H_4COOC_2H_5\text{-}4)_5H$

As indicated in the below Scheme 3, 200 mg of $C_{60}$ was dissolved in 10 mL of orthodichlorobenzene under nitrogen atmosphere. To the mixture: 15 equivalents of 4-ethoxycarbonylphenyl zinc iodide reagent 4-IZnPhCO$_2$Et in THF solution (concentration: about 0.5 M) as the organometallic reagent (A); and 15 equivalents of copper (I) bromide-dimethylsulfide complex CuBr.S(CH$_3$)$_2$ as the copper compound (B) were added at 0° C. After that, the mixture was heated to 25° C. and reaction was performed. 3 hours later, 0.5 mL of saturated ammonium chloride solution was added to the mixture, and the reaction was terminated. The reaction product was diluted by adding 5 mL of deaerated toluene, and was passed through a short-pass silica gel column using ethyl acetate as a developing solvent to remove by-products such as zinc salt. The solvent was distilled away, and 50 mL of methanol was added. A solid obtained from reprecipitation was subjected to filtration, and thereafter it was washed with methanol to obtain 395 mg of penta(organo)[60] fullerene derivative $C_{60}(C_6H_4COOC_2H_5\text{-}4)_5H$ (isolated yield: 97%).

Scheme 3

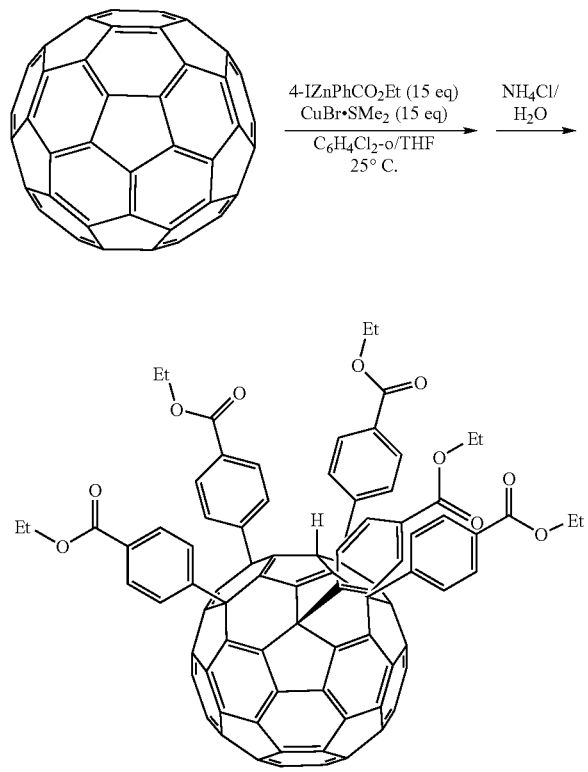

NMR, IR and APCI-MS data of the obtained product are as follows:

$^1$H NMR (CDCl$_3$): δ 1.40 (m, 15H, 5CH$_3$), 4.40 (m, 10H, 5CH$_2$), 5.34 (s, 1H, C$_{60}$H), 7.42 (d, J=8.00 Hz, 2H, ArH), 7.64 (d, J=8.00 Hz, 4H, ArH), 7.83 (d, J=8.00 Hz, 2H, ArH), 7.84 (d, J=8.00 Hz, 4H, ArH), 7.88 (d, J=8.00 Hz, 4H, ArH), 8.03 (d, J=8.00 Hz, 4H, ArH).

$^{13}$C NMR (CDCl$_3$): δ 14.07 (1C, CH$_3$), 14.28 (2C, 2CH$_3$), 14.32 (2C, 2CH$_3$), 58.55 (2C, 2C$_{60}$(C$_\alpha$)), 58.72 (1C, C$_{60}$(C$_\alpha$)), 60.74 (2C, 2C$_{60}$(C$_\alpha$)), 61.17 (3C, 3CH$_2$), 61.26 (2C, 2CH$_2$), 62.72 (1C, CO$_{60}$(CH)), 127.39, 127.64, 127.66, 129.67, 129.97, 130.15, 130.21, 130.35, 130.44, 143.21, 143.23, 143.89, 143.94, 143.97, 144.10, 144.17, 144.25, 144.38, 144.93, 145.23, 145.31, 145.33, 146.72, 146.92, 147.00, 147.63, 147.98, 148.13, 148.27, 148.56, 148.64, 148.68, 149.60, 150.64, 151.50, 152.57, 155.27, 165.84 (1C, CO$_2$Et), 165.93 (2C, 2CO$_2$Et), 165.95 (2C, 2CO$_2$Et).

IR (powder, cm$^{-1}$): 2977 (m, $v_{C-H}$), 1694 (m, $v_{C=O}$), 1607 (s), 1409 (s), 1258 ($v_{C-O}$), 1181 (s).

APCI-MS (−): m/z 1466 (M$^-$). APCI-HRMS (−): calcd. for $C_{105}H_{45}O_{10}$ (M$^-$-H) 1465.3013, found 1465.2966.

Example 3

Production of $C_{60}(CH_2CO_2\text{-}1\text{-hexyl})_5H$ 1.0 mL of THF and 9.0 μL of 1,2-dibromoethane were added to zinc powder (196 mg, 3.0 mmol) under nitrogen atmosphere to be heated to reflux. To the mixture, 2 drops of trimethylchlorosilane were added to perform zinc activation treatment, and thereafter 15 equivalents of (1-hexyl)bromoacetate (335 mg, 1.5 mmol) was added to the mixture, which was stirred at room temperature for 2 hours to prepare an organozinc reagent.

After that, as indicated in the below Scheme 4, to 15 equivalents of the above-described organozinc reagent, 15 equivalents of copper (1) bromide-dimethylsulfide complex CuBr.SMe$_2$ (308 mg, 1.5 mmol), 15 equivalents of N,N-dimethylimidazolidinone (0.16 mL, 1.5 mmol), 1.0 mL of THF and C$_{60}$ in 1,2-dichlorobenzene solution (C$_{60}$: 72.0 mg, 1,2-dichlorobenzene: 5 mL) were added under nitrogen atmosphere, and the mixture was reacted at 40° C. 1 hour later, 0.1 mL of saturated ammonium chloride solution was added to the mixture, and the reaction was terminated. The reaction product was diluted by adding 10 mL of deaerated toluene, and was passed through a short-pass silica gel column using toluene firstly and ethyl acetate secondly as developing solvents to remove by-products such as zinc salt. The solvents were distilled away, and 100 mL of methanol was added. A solid obtained from reprecipitation was subjected to filtration, and thereafter it was washed with methanol to obtain $C_{60}(CH_2CO_2\text{-}1\text{-hexyl})_5H$ (isolated yield: 91%).

Scheme 4

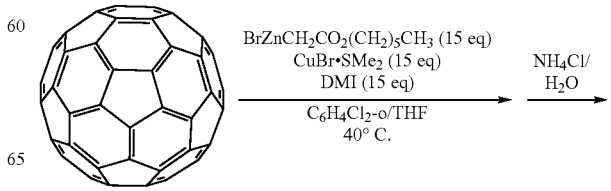

-continued

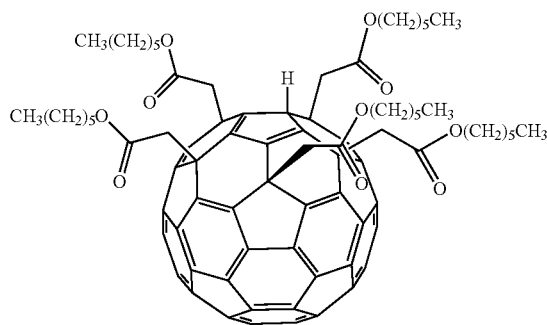

NMR data of the obtained product are as follows:

$^1$H NMR (CDCl$_3$, 500 MHz) δ 5.16, 4.20 (t, J=6.6 Hz, 2H), 4.17 (t J=6.5 Hz, 2H), 4.14 (t, J=6.7 Hz, 2H), 3.711 (s, 2H), 3.707 (d, J=14.6 Hz, 2H), 3.61 (d, J=14.6 Hz 2H), 3.54 (d, J=14.6 Hz, 2H), 3.51 (d, J=14.61 Hz, 2H), 1.67-1.55 (m, 10H), 1.35-1.20 (m, 30H), 0.90-0.84 (t overlapped, 15H); $^{13}$C{$^1$H} NMR (CDCl$_3$, 125 Hz) δ 171.31 (1C, CO), 170.51 (2C, CO), 169.91 (2C, CO), 155.20 (2C), 153.36 (2C), 152.19 (2C), 150.54 (2C), 148.62 (2C), 148.55 (2C), 148.51 (2C), 148.21 (2C), 148.01 (2C), 147.97 (1C), 147.83 (2C), 147.60 (2C), 147.01 (2C), 146.90 (2C), 146.82 (1C), 146.53 (2C), 145.45 (2C), 145.13 (2C), 145.00 (2C), 144.56 (2C), 144.11 (2C), 143.98 (2C), 143.82 (2+2C), 143.74 (2C), 143.66 (2C), 143.64 (2C), 142.72 (2C), 65.37 (1+2C, COCH2CH2-), 65.31 (2C, COCH2CH2-), 57.61 (1C), 53.78 (2C), 52.37 (1C), 51.56 (2C), 44.69 (1+2C, C60CH2CO), 44.10 (2C, C60 CH2CO), 31.39 (1+2C, CH2), 31.37 (2C, CH2), 28.54 (2C, CH2), 28.50 (1+2C, CH2), 25.56 (2C, CH2), 25.54 (1+2C, CH2), 22.52 (1+2C, CH2), 22.50 (2C, CH2), 13.99 (1+2C, —CH3), 13.98 (2C, —CH3).

Example 4

Production of C$_{60}$(CH$_2$CO$_2$CH$_2$C$_6$H$_5$)$_5$H

An organozinc reagent was prepared in a manner similar to that in Example 3 except that benzyl bromoacetate (344 mg) was used instead of (1-hexyl)bromoacetate.

After that, as indicated in the below Scheme 5, C$_{60}$(CH$_2$CO$_2$CH$_2$C$_6$H$_5$)$_5$H was obtained in a manner similar to that in Example 3 except that the obtained organozinc reagent was used (isolated yield: 89%).

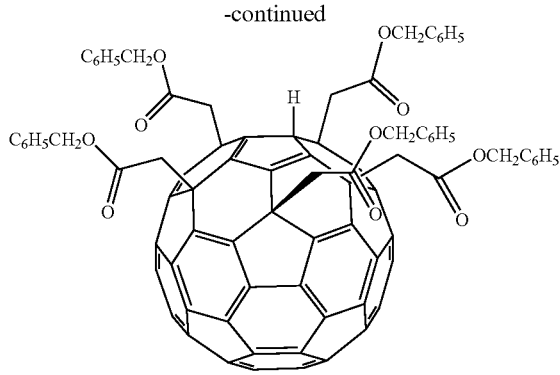

NMR and APCI-MS data of the obtained product are as follows:

$^1$H NMR (CDCl$_3$, 500 MHz) δ 7.32-7.23 (m, 25H), 5.19-5.09 (overlapped d, CH$_2$C$_6$H$_5$, 8H), 5.13 (s, overlapped, CpH and CH$_2$C$_6$H$_5$, 2+1H), 3.69 (d, J=14.3 Hz, 2H), 3.68 (s, 2H), 3.59 (d, J=14.3 Hz, 2H), 3.56 (d, J=14.3 Hz, 2H), 3.50 (d, J=14.3 Hz, 2H); $^{13}$C{$^1$H} NMR (CDCl$_3$, 125 Hz) δ 171.08 (1C, CO), 170.29 (2C, CO), 169.67 (2C, CO), 155.02 (2C), 153.35 (2C), 152.00 (20), 150.38 (20), 148.60 (2C), 148.53 (2C), 148.46 (2C), 148.16 (2C), 147.97 (2C), 147.93 (1C), 147.79 (2C), 147.56 (2C), 146.96 (2C), 146.84 (2C), 146.77 (1C), 146.32 (2C), 145.25 (2C), 144.95 (2C), 144.87 (2C), 144.38 (2C), 144.10 (2C), 143.81 (2C), 143.79 (2C), 143.74 (2C), 143.66 (2C), 143.64 (2C), 143.55 (2C), 142.73 (2C), 137.83 (C$_6$H$_5$, 1C), 135.38 (C$_6$H$_5$, 2C), 135.28 (C$_6$H$_5$, 2C), 128.56 (C$_6$H$_5$, 2C), 128.55 (C$_6$H$_5$, 4C), 128.53 (C$_6$H$_5$, 4C), 128.52 (C$_6$H$_5$, 4C), 128.47 (C$_6$H$_5$, 1+2+2C), 128.39 (C$_6$H$_5$, 2C), 128.37 (C$_6$H$_5$, 4C), 66.92 (CH$_2$C$_6$H$_5$, 2C), 66.91 (CH$_2$C$_6$H$_5$, 1C), 66.87 (CH$_2$C$_6$H$_5$, 2C), 57.66 (1C), 53.68 (2C), 52.30 (1C), 51.48 (2C), 47.24 (1C), 44.44 (2C), 43.92 (2C).

MS (APCI-): m/z 1465 (M-H)$^-$; HRMS (APCI-) m/z calcd for C$_{105}$H$_{45}$O$_{10}$ (M-H), 1465.3013; found 1465.3030.

Example 5

Production of C$_{60}$(CH$_2$CO$_2$CH$_2$CF$_3$)$_5$H

An organozinc reagent was prepared in a manner similar to that in Example 3 except that 2,2,2-trifluoroethyl bromoacetate (331 mg) was used instead of (1-hexyl)bromoacetate.

After that, as indicated in the below Scheme 6, C$_{60}$(CH$_2$CO$_2$CH$_2$CF$_3$)$_5$H was obtained in a manner similar to that in Example 3 except that the obtained organozinc reagent was used (isolated yield: 59%).

Scheme 5

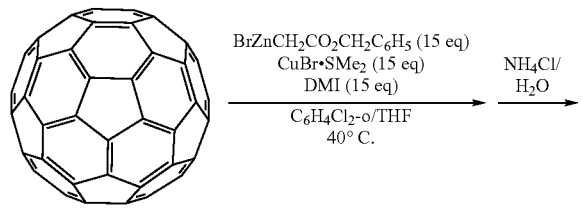

Scheme 6

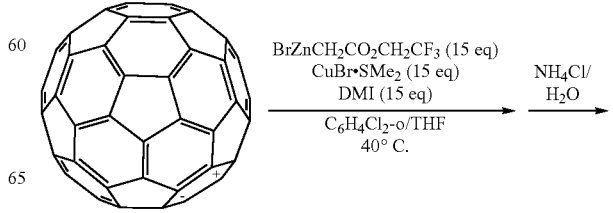

-continued

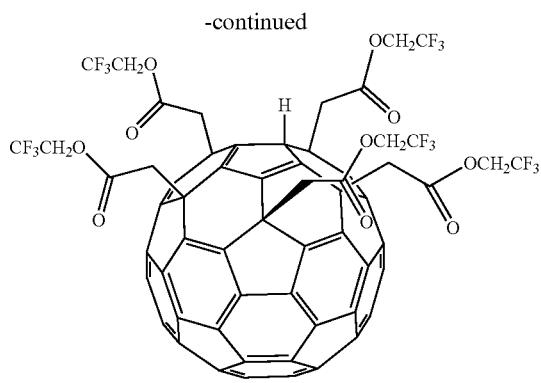

NMR and APCI-MS data of the obtained product are as follows:

$^1$H NMR (CDCl$_3$, 500 MHz) δ 5.12 (s, 1H), 4.65-4.52 (m, 10H, CH$_2$CF$_3$), 3.90 (s, 2H), 3.89 (d, J=15.5 Hz, 2H), 3.74 (d, J=14.6 Hz, 2H), 3.73 (d, J=15.5 Hz, 2H), 3.66 (d, J=14.6 Hz, 2H); $^{13}$C{$^1$H} NMR (CDCl$_3$, 125 Hz) δ 169.95 (1C, CO), 169.11 (2C, CO), 168.29 (2C, CO), 154.83 (2C), 153.49 (2C), 151.75 (2C), 149.77 (2C), 148.84 (2C), 148.77 (2C), 148.66 (2C), 148.38 (2C), 148.15 (2C+1C), 147.99 (2C), 147.76 (2C), 147.06 (2C), 146.98 (2C), 146.88 (1C), 145.87 (2C), 145.00 (2C), 144.77 (2C), 144.65 (2C), 144.38 (2C), 144.00 (2C), 143.93 (2C), 143.87 (2), 143.82 (2C), 143.80 (2C), 143.51 (2C), 143.34 (2C), 143.00 (2C), 122.72 (q, $^1$J$_{CF}$=277.3 Hz, 1C+2C), 122.69 (q, $^1$J$_{CF}$=277.3 Hz, 2C), 60.80 (q, $^2$J$_{CF}$=37.0 Hz, 2C), 60.77 (q, $^2$J$_{CF}$=36.9, 1C), 60.75 (q, $^2$J$_{CF}$=36.8 Hz, 2C), 57.84 (1C), 53.22 (2C), 51.94 (1C), 51.05 (2C), 46.33 (1C) 43.75 (2C), 43.10 (2C); $^{19}$F NMR (CDCl$_3$, 500 MHz) δ−73.59 (s, 15F).

MS (APCI-): m/z 1425 (M-H)$^-$; HRMS (APCI-) m/z calcd for C$_{80}$H$_{20}$F$_{15}$O$_{10}$ (M-H), 1425.0817; found 1425.0825.

INDUSTRIAL APPLICABILITY

The fullerene derivative obtained in the present invention can be utilized as an electronic material, a physiologically active substance, a ligand of a metal complex and the like. Further, the fullerene derivative obtained in the present invention can be used as an intermediate for synthesizing various types of fullerene derivatives by additional conversion reaction.

The invention claimed is:

1. A method for producing a fullerene derivative comprising reacting:
   a fullerene;
   an organometallic reagent (A) comprising: a substituted or unsubstituted alkyl group, a substituted or unsubstituted alkenyl group, a substituted or unsubstituted alkynyl group, a substituted or unsubstituted aryalkyl group or a substituted or unsubstituted aryl group; and B, Al, Zn, Sn, Pb, Te, Ti, Mn, Zr or Sm; and
   a copper compound (B).

2. A method for producing a fullerene derivative comprising reacting:
   a fullerene;
   an organometallic reagent (A) comprising: a substituted or unsubstituted alkyl group, a substituted or unsubstituted alkenyl group, a substituted or unsubstituted alkynyl group, a substituted or unsubstituted aryalkyl group or a substituted or unsubstituted aryl group; and Al, Zn, Sn or Pb; and
   a copper compound (B).

3. A method for producing a fullerene derivative comprising reacting:
   a C$_{60}$ fullerene;
   an organometallic reagent (A) comprising: an alkyl group which may have one or more substituents selected from the group consisting of an ester group, an amide group, a cyano group and a halogen atom, an alkenyl group which may have one or more substituents selected from the group consisting of an ester group, an amide group, a cyano group and a halogen atom, or an aryl group which may have one or more substituents selected from the group consisting of an ester group, an amide group, a cyano group and a halogen atom; and Zn; and
   a monovalent or divalent copper compound (B).

4. The method for producing a fullerene derivative according to claim 1, wherein the fullerene derivative is represented by the following formula (1):

$$Cn(R^4)_m(R^5)_p \qquad (1)$$

wherein n is an even number of 60 or more; m is an integer from 3 to 10; p is 1 or 2; each R$^4$ is independently a hydrogen atom, a substituted or unsubstituted C$_1$-C$_{20}$ hydrocarbon group, a substituted or unsubstituted C$_1$-C$_{20}$ alkoxy group, a substituted or unsubstituted C$_6$-C$_{20}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group); and R$^5$ is a hydrogen atom or a C$_1$-C$_{20}$ hydrocarbon group.

5. The method for producing a fullerene derivative according to claim 1, wherein the fullerene derivative is a fullerene derivative C$_{60}$(R$^4$)$_5$R$^5$ represented by the following formula (2):

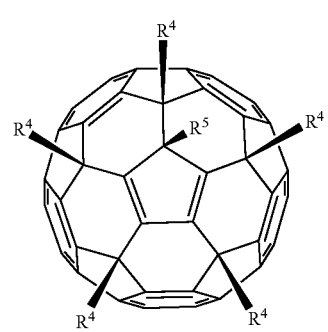

wherein each R$^4$ is independently a hydrogen atom, a substituted or unsubstituted C$_1$-C$_{20}$ hydrocarbon group, a substituted or unsubstituted C$_6$-C$_{20}$ alkoxy group, a substituted or unsubstituted C$_6$-C$_{20}$ aryloxy group, a substituted or unsubstituted amino group, a substituted or unsubstituted silyl group, a substituted or unsubstituted alkylthio group (—SY$^1$: in the formula, Y$^1$ is a substituted or unsubstituted C$_1$-C$_{20}$ alkyl group), a substituted or unsubstituted arylthio group (—SY$^2$: in the formula, Y$^2$ is a substituted or unsubstituted C$_6$-C$_{18}$ aryl group), a substituted or unsubstituted alkylsulfonyl group (—SO$_2$Y$^3$: in the formula, Y$^3$ is a substituted or unsubstituted C$_1$-C$_{20}$ alkyl group), or a substituted or unsubstituted arylsulfonyl group (—SO$_2$Y$^4$: in the formula, Y$^4$ is a substituted or unsubstituted C$_6$-C$_{18}$ aryl group); and R$^5$ is a hydrogen atom or a C$_1$-C$_{20}$ hydrocarbon group.

6. The method for producing a fullerene derivative according to claim 4, wherein R$^4$ has one or more substituents selected from the group consisting of an ester group, a carboxyl group, an amide group, an alkyne group, a trimethylsilyl group, a trimethylsilylethynyl group, an aryl group, an amino group, a phosphonyl group, a thio group, a carbonyl group, a nitro group, a sulfo group, an imino group, a halogeno group, and an alkoxy group.

7. The method for producing a fullerene derivative according to claim 4, wherein R$^4$ has one or more substituents selected from the group consisting of an ester group, an amide group, an alkyne group, a trimethylsilyl group, a trimethylsilylethynyl group, and an aryl group.

8. The method for producing a fullerene derivative according to claim 4, wherein R$^5$ is a hydrogen atom or a C$_1$-C$_{20}$ alkyl group.

9. The method for producing a fullerene derivative according to claim 4, wherein the fullerene derivative is represented by the following formula (3):

(3)

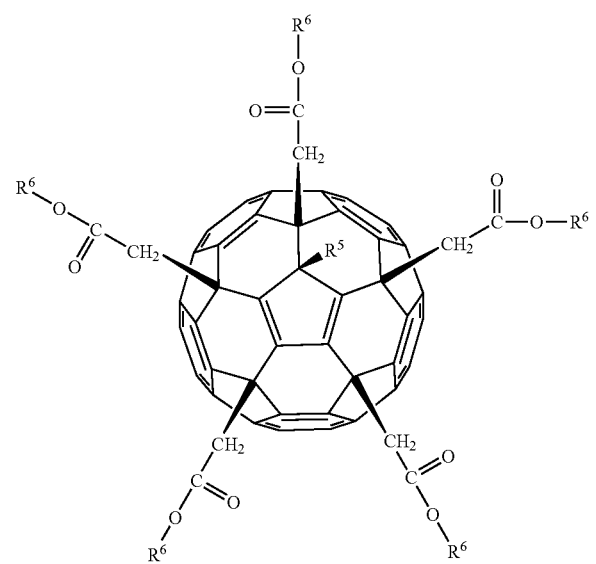

wherein R$^5$ is a hydrogen atom or a substituted or unsubstituted C$_1$-C$_{20}$ hydrocarbon group; and each R$^6$ is independently a hydrogen atom or a substituted or unsubstituted C$_1$-C$_{20}$ hydrocarbon group.

10. The method for producing a fullerene derivative according to claim 9, wherein R$^5$ is a hydrogen atom or a substituted or unsubstituted C$_1$-C$_{20}$ alkyl group.

11. The method for producing a fullerene derivative according to claim 9, wherein R$^6$ is a hydrogen atom, a substituted or unsubstituted C$_1$-C$_{20}$ alkyl group, a substituted or unsubstituted C$_2$-C$_{20}$ alkenyl group, or a substituted or unsubstituted C$_2$-C$_{20}$ alkynyl group.

12. The method for producing a fullerene derivative according to claim 1, wherein an organic group included in the organometallic reagent (A) is a methyl group, an ethyl group, an isopropyl group, a butyl group or a phenyl group.

13. The method for producing a fullerene derivative according to claim 1, wherein the copper compound (B) is CuBr.S(CH$_3$)$_2$.

14. A fullerene derivative represented by the following formula (3):

(3)

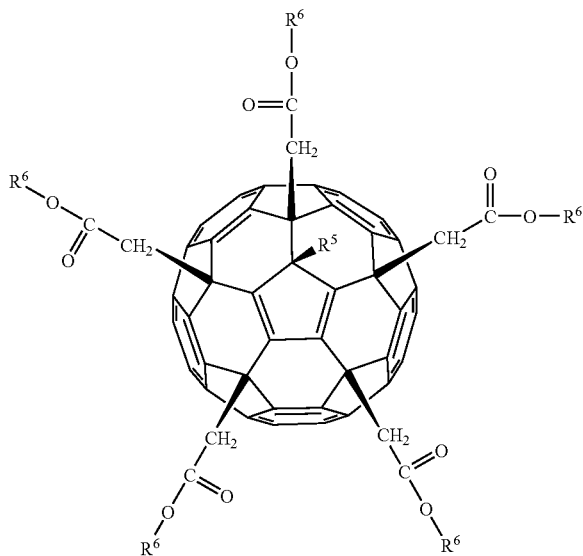

wherein R$^5$ is a hydrogen atom or a substituted or unsubstituted C$_1$-C$_{20}$ hydrocarbon group; and each R$^6$ is independently a hydrogen atom or a substituted or unsubstituted C$_1$-C$_{20}$ hydrocarbon group.

15. The fullerene derivative according to claim 14, wherein R$^5$ is a hydrogen atom or a substituted or unsubstituted C$_1$-C$_{20}$ alkyl group.

16. The fullerene derivative according to claim 14, wherein R$^6$ is a hydrogen atom, a substituted or unsubstituted C$_1$-C$_{20}$ alkyl group, a substituted or unsubstituted C$_2$-C$_{20}$ alkenyl group, or a substituted or unsubstituted C$_2$-C$_{20}$ alkynyl group.

17. A fullerene derivative represented by the following formula (4):

(4)

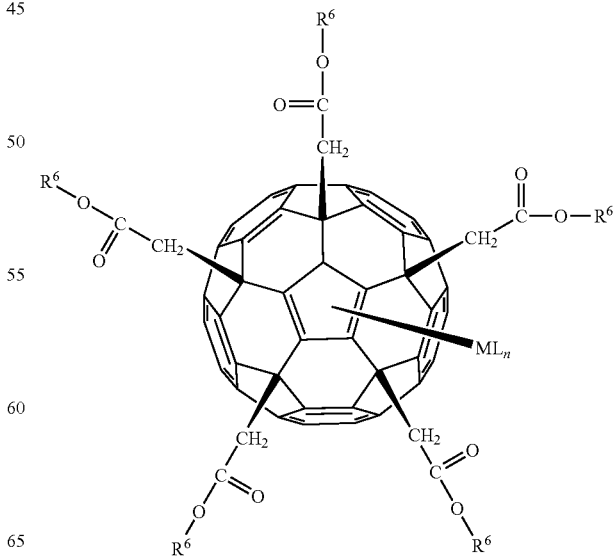

wherein each $R^6$ is independently a hydrogen atom or a substituted or unsubstituted $C_1$-$C_{20}$ hydrocarbon group; M is a metallic atom; L is a ligand of M; and n is the number of Ls.

18. The fullerene derivative according to claim 17, wherein $R^6$ is a hydrogen atom, a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group.

19. The fullerene derivative according to claim 17, wherein M is a transition metal.

20. The fullerene derivative according to claim 17, wherein M is a group 8-10 transition metal.

21. The fullerene derivative according to claim 17, wherein: M is Fe, Ru, or Os; n is an integer from 0 to 5; and L is a halogen atom, alkoxy group, alkyl group, alkyne group or cyclopentadienyl group.

\* \* \* \* \*